(12) United States Patent
Kaplan

(10) Patent No.: US 6,443,921 B1
(45) Date of Patent: Sep. 3, 2002

(54) CARPAL TUNNEL PROTECTOR

(75) Inventor: Hyman I. Kaplan, Lincolnwood, IL (US)

(73) Assignees: Evelyn Kaplan, Lincolnwood, IL (US); Robert D. Kaplan, Scottsdale, AZ (US)

( * ) Notice: Subject to any disclaimer, the term of this patent is extended or adjusted under 35 U.S.C. 154(b) by 204 days.

(21) Appl. No.: 09/130,904

(22) Filed: Aug. 7, 1998

(51) Int. Cl.$^7$ .............. A61F 13/00; A61F 5/00; A41D 19/00
(52) U.S. Cl. .............. 602/64; 602/21; 602/60; 2/161.7
(58) Field of Search .............. 602/5, 13, 20, 602/21, 22, 60, 61, 62, 63, 64; 128/856, 877, 878, 879, 880; 2/159–161.8, 16, 17, 21, 161.1, 161.6, 162, 170; D2/610, 616, 617, 623

(56) References Cited

U.S. PATENT DOCUMENTS

| | | | | |
|---|---|---|---|---|
| 2,567,489 A | * | 9/1951 | Lewis | 2/20 |
| 3,416,518 A | * | 12/1968 | Samuels et al. | 2/16 X |
| 3,648,291 A | * | 3/1972 | Pankers | 2/16 |
| 3,786,804 A | * | 1/1974 | Lewis | 602/16 |
| 4,832,010 A | * | 5/1989 | Lerman | 602/26 |
| 4,901,372 A | * | 2/1990 | Eberbach | 602/21 |

OTHER PUBLICATIONS

Webster's II New Riverside University Dictionary, p. 486, 1984.*

* cited by examiner

Primary Examiner—Kim M. Lewis
(74) Attorney, Agent, or Firm—Paul H. Gallagher

(57) ABSTRACT

A glove for preventing carpal tunnel syndrome. It includes a flexible open-ended sleeve with a side thumb hole. It has a cushion on the inner surface of the front of the glove, which covers the carpal tunnel area. The sleeve is highly yieldable and elastic and is essentially of single thickness throughout.

1 Claim, 2 Drawing Sheets

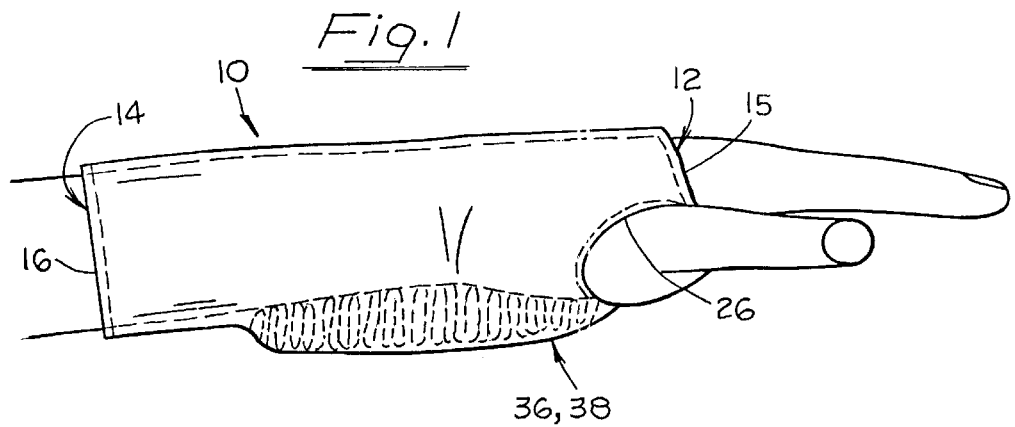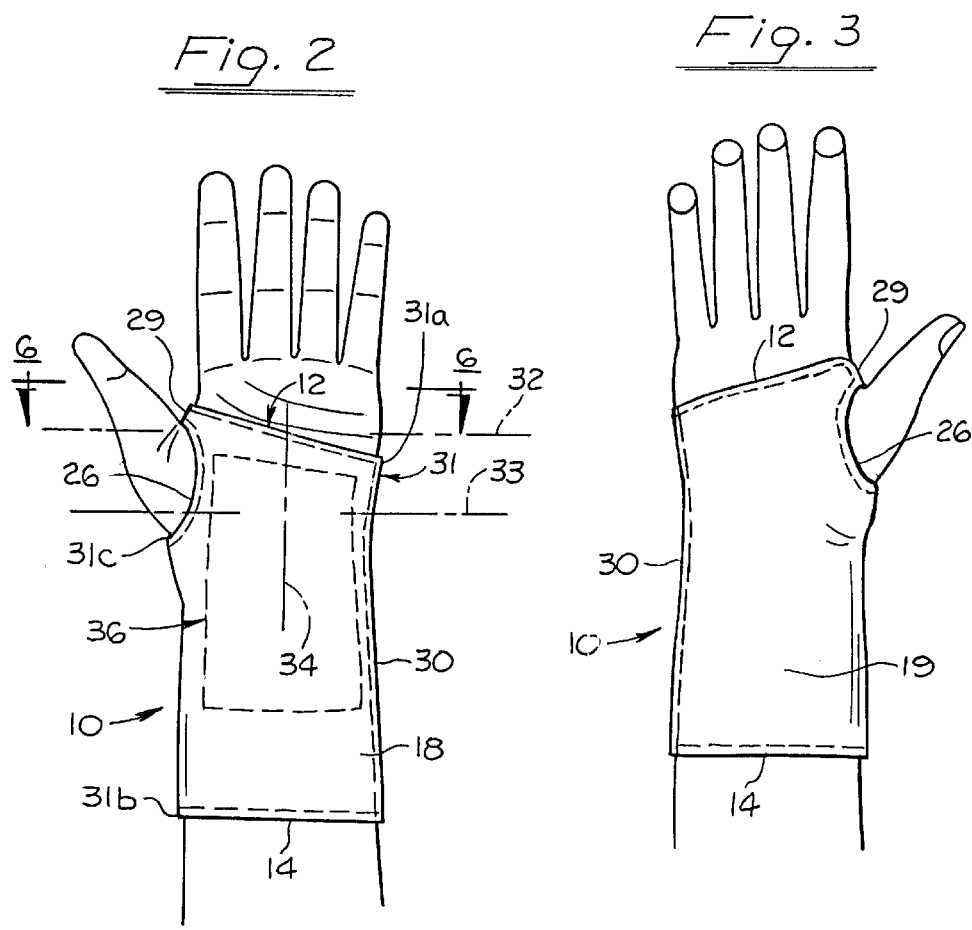

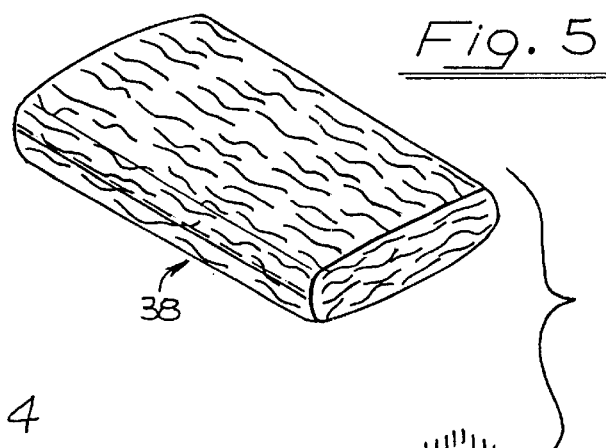
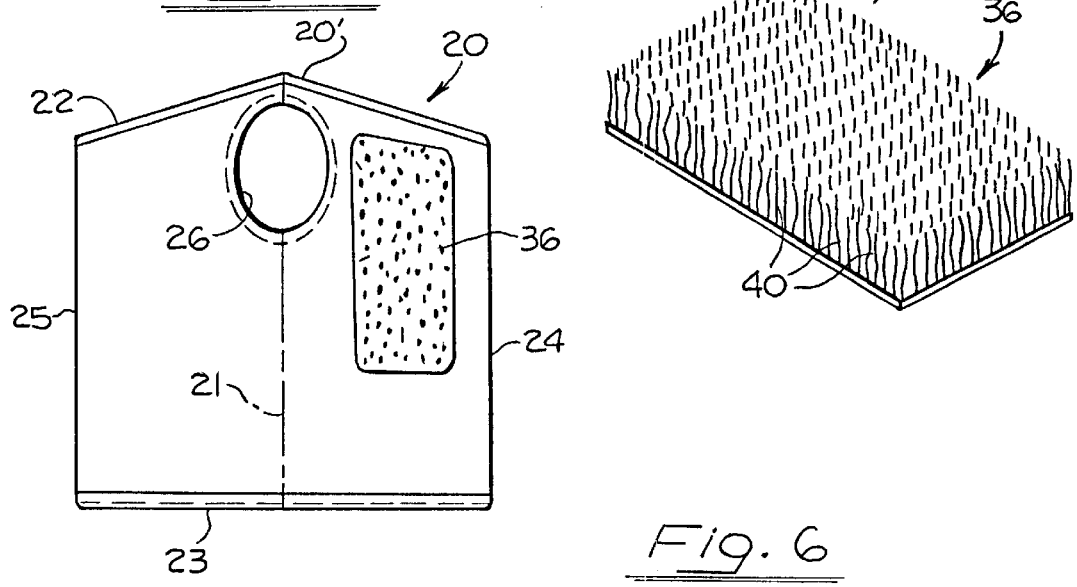
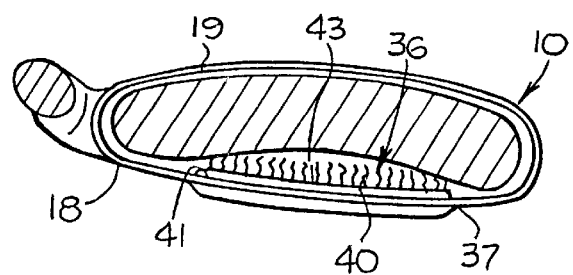
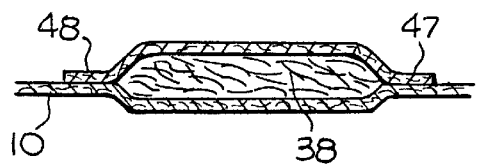

US 6,443,921 B1

CARPAL TUNNEL PROTECTOR

FIELD OF THE INVENTION

The present invention relates to a protector for preventing the occurrence of carpal tunnel syndrome.

BACKGROUND OF THE INVENTION

Carpal tunnel syndrome is a very common ailment, resulting from repeated particular movements and activity of the fingers and hand in certain occupations.

The carpal tunnel leads from the wrist, forwardly between the ball of the thumb and the heel of the hand and into the area of the palm or metacarpus. Nerves from the arm extend through the carpal tunnel and lead to the fingers.

A transverse ligament extends between the ball of the thumb and the heel of the hand, over the nerves, forming the tunnel.

The ailment is associated particularly with certain occupations, including operators of various keyboards, such as in typewriters and computers, and other instruments in secretarial work.

Included in this kind of operations, are repeated motions of the fingers and the hand, which in many cases are repeated a great number of times, even in the course of one day. When they are repeated again in and throughout an extended period of time, such as months, and years, serious damage is done to the nerves in the tunnel. Specifically, scar tissue is developed on the ligament and adjacent tissue, causing irritation and eventual constriction of the median nerve. This results in the onset of subjective symptom of tingling, numbness, pain and eventual limitation of movement of the fingers affected.

It is found also that in addition to strikes against the carpal tunnel, merely rubbing the hand or wrist over a flat surface or deck, over an extended period of time, causes the same damage as that produced by hits or strikes. For example in using a computer, the operator grasps the mouse and moves it around, and in this operation, the base of the palm of the hand as well as the wrist, move over the deck, and drags on it. This movement and dragging effect produces carpal tunnel syndrome.

Computers are being used by an increasingly greater number of people, beginning at an early age, even in school, and regularly even at the age of 5 years. They are popularized so that nearly every child is urged to use them, or, as in school, required to use them, and they continue to use them in the home. Thus the cause of the trouble or ailment begins early in life of the person, and continues for many years.

The use of the computer is a further inducement for the younger generation to utilize the preventative properties of the device of the present invention. The device uses a cushion of medical shearling sheepskin or polyester foam, that are resilient and even absorb the shock of repeated trauma and still maintain their resilience after repeated washings.

There have been attempts made, in the past, to prevent the damage to the carpal nerves, but they have been found ineffective. A particular objection to such prior devices is that they are most often very stiff, and confining, and in general prohibit the free use of the hand. In secretarial occupations referred to, it is necessary that the hand be completely free to move in all directions, and with great agility, and if that complete freedom is not achieved, the protective devices are unsuccessful.

Certain of the prior devices intended for prevention of the syndrome have even caused other pains that otherwise may not have occurred. Some of the devices are quite heavy, and cause fatigue over long periods of use.

Still another objection to the various prior devices used, had to do with a condition of ventilation or breathing of the device. It is necessary that the protective device also enable free movement of air therethrough to prevent the build up of heat and perspiration. These two phenomenons cause great discomfort to the user, particularly when used over extended periods of time.

Still further, many prior devices are not washable, or at least not to a practical extent, and upon repeated washings, they become ineffective for the purpose intended. Those prior devices most often were very expensive, and when they become soiled, the user is tempted to discard them and buy new devices, which results in undesirable greater cost.

SUMMARY OF THE INVENTION

A broad object of the invention is to provide a device for originally preventing carpal tunnel syndrome, and, in cases where it is already present, to prevent further progression of it.

Another object is to provide such a device, having the following specific features and advantages:

1. The device is in the form of a sleeve that is easily pulled over the hand of the user, into its intended position of use.
2. The sleeve is stretchable and yieldable, enabling the users hand to be bent and manipulated with great freedom.
3. When in useable position, the front end of the sleeve is positioned about the middle of the palm, and has engagement with the thumb to prevent its being moved too far when it is applied to the hand, that the thumb and fingers being uncovered, are completely free and exposed, and free to be moved in any and all directions.
4. The sleeve is of woven material, and very porous to enable complete ventilation, enabling air and moisture to pass freely through.
5. It includes a cushion that is resilient, and when the device is applied to the hand, rests over the carpal tunnel and adjacent portions to assure that the carpal tunnel is completely covered, while maintaining freedom of movements of the hand referred to above.
6. The device is completely washable, repeatedly, without damage thereto.
7. It can be applied to the hand by very simple movements, similarly to pulling a mitten or glove over the hand.

BRIEF DESCRIPTIONS OF THE FIGURES OF THE DRAWINGS

FIG. 1 is a side view of the device applied to the hand.
FIG. 2 is an under view.
FIG. 3 is a top view.
FIG. 4 is a view of a flat piece of material from which the device is made.
FIG. 5 is a perspective view showing different types of protective pads.
FIG. 6 is cross-sectional view of the device as viewed at line 6—6 of FIG. 2.
FIG. 7 is similar to the lower central part of FIG. 6, showing an alternate form of construction.

DETAILED DESCRIPTION OF THE DRAWINGS

The device as a whole is indicated at 10. It is in the form of a sleeve or tube, having a front end 12 and a rear end 14, and correspondingly a front opening 15, and a rear opening 16. The sleeve is flexible, as referred to again below, and when in relaxed condition as lying on a flat surface, it lies flat, in doubled condition, forming a front leaf 18 and a back leaf 19.

The sleeve is formed from a single flat piece of material 20 (FIG. 4), folded over on a central longitudinal line 21. For identification purposes, the flat piece 20 has a front end 22, and a rear end 23, corresponding to the front and rear ends 12, 14 of the sleeve. It also has side edges 24, 25.

The flat piece 20 is nearly rectangular, but having inclined front end edges leading up to a central point 20'.

A thumb hole 26 is cut in the piece, and then elastic binding strips 31 are sewn over the edge of the thumb hole and the front and rear end edges, identified individually as 31a, 31b, 31c. The pieces 31a and 31c are of ¼" size in width, and the piece 31b, ½" in width. These binding strips also are of soft elastic and yieldable material, enabling stretching corresponding to the transverse stretching of the material of the sleeve.

FIG. 4 also shows a cushion 36 sewn in place at one side of the piece 20, on what becomes the inner surface of the piece when the latter is folded. It is located on one side or the other, relative to the thumb hole, as to whether it is for the right or left hand.

The thumb hole 26 is adjacent to, but spaced from, the front end, forming a connector segment 29, which engages the thumb, when the sleeve is applied to the hand, as referred to again below.

The side edges 24, 25 are stitched together at 30 (FIGS. 2, 3) forming the tubular sleeve, the resulting sleeve, when lying flat, being nearly in the form of a rectangle, but having an inclined front end. The material of the sleeve is preferably NYLON-LYCRA which is highly stretchable and elastic in both directions, and is highly pervious to air and moisture. It may be woven or knitted, and is uniform in construction in transverse directions, around the sleeve.

For the purpose of referencing the sleeve to the hand, when fitted thereon, FIG. 2 includes axes 32, 33, 34: 32 a transverse axis through the palm or metacarpus; 33 a transverse axis through the rear end of the palm and substantially centrally of the carpal tunnel; 34 a substantially centrally longitudinally axis through the carpal tunnel.

The cushion 36 preferably is of rectangular shape stitched to the sleeve at 38 in such location as to cover the carpal tunnel.

One form of cushion (36) is preferably of medically treated sheep skin. The sheepskin wool has hairs or filaments 40 leading from a backing 41 which in the case of natural wool is the skin. In the pretreatment of the wool, the filaments are put in straight and spaced position and the skin is softened.

Except for the binding strips 31, no further structural elements or members in addition to the woven material, are utilized for completing the sleeve. The binding strips do not affect the condition of the sleeve proper, that is, the body of the sleeve, from its full and complete flexibility and adaptation to the hand of the wearer. The complete flexibility and yieldability of the sleeve enables the hand to be manipulated with complete freedom and without any restriction.

As shown in FIGS. 1, 2, 4, the cushion 36 is located at the fore end of the sleeve or tube, with its front end closely adjacent the front end 12 of the sleeve, and its rear end spaced somewhat from the rear end 14 of the sleeve. In the case shown, the cushion is of a length slightly more than one-half the length of the sleeve, this relationship being of importance in connection with location of the cushion relative to the carpal tunnel.

The device or sleeve is applied to the hand by inserting the hand into the rear end 14 thereof and through the sleeve, and extending it to the exterior at the front end 12. The sleeve in so applying it is pulled onto the hand as is a glove or mitten. In this step, the thumb is extended outwardly through the side thumb hole 26, and upon continued pulling of the sleeve, a connector segment 29 engages the inner end of the thumb. This limits the extent to which the sleeve can be pulled onto and over the hand to its active position. This position is shown in FIGS. 2, 3, where the front end is closely adjacent the axis 32, although it is at a slight angle thereto. Referring again to the location of the cushion, in the setting shown and described, and with the sleeve in fitted position, the cushion lies entirely over the carpal tunnel, with the carpal tunnel disposed substantially midway of the length of the cushion. Thus the carpal tunnel is completely covered, considered in longitudinal direction, and the end portions of the cushion extend beyond the carpal tunnel in respective directions, sufficiently to assure complete coverage of the carpal tunnel. This position is represented by the transverse axis 33. The rear end of the sleeve, i.e. beyond the cushion, may be so dimensioned as to extend onto the wrist or forearm to an extent desired to assure complete coverage of the hand.

When the sleeve is in such fitted position, the fore part of the hand, or metacarpus, is completely exposed, as are all the fingers and the thumb. The elastic binding strips 31a, 31c yield in response to flexing the hand, and the fingers and thumb, being completely exposed to the exterior, are therefore completely free and manipulable, this condition being enabled by the yieldability of both the binding strip 31a and the material of the sleeve itself. In association with this manipulation of the fingers and thumb, and the front end of the sleeve, the rear portion of the sleeve, being highly flexible and yieldable, enables complete manipulation of the hand and wrist rearwardly of the thumb. Thus the entire device is of such character as to enable full and free manipulation of the metacarpus and fingers and thumb, as well as the wrist. There are no wrap-around features involved, such as would produce undue stiffness and binding effects on the hand.

In this full fitted position of the device, the cushion is of course completely fitted over the carpal tunnel as stated, and when the user drops his hand onto a supporting surface, the strike or impact is not directed fully to the carpal tunnel, as it was heretofore, but is transmitted into the cushion, and thus distributed throughout the cushion, and diverted, with very slight or no impact on the carpal tunnel.

It is to be noted that the cushion does not in any way restrict free movement of the hand. The cushion is on the inner or concave side of the hand, and lies substantially flat when the hand is flat, and when the hand is manipulated, it is so moved that the inner side of the hand becomes somewhat concave tending to enclose the cushion. This is in contrast to a condition where the cushion itself may impede the free movements of the hand.

As noted above the material of the sleeve, as well as the filaments of the wool, are porous, enabling free and full movement of air and moisture therethrough, keeping the entire device dry, and relatively free of perspiration. It does not create heat or retain moisture. The binding strips are elastic and operable for yieldingly holding the sleeve against the hand and wrist of the bearer.

Considering the concave shape of the hand (FIG. 6), it will be noted that on the front or concave side of the hand, the binding strip 31a does not fit tightly against the palm, but is slightly lifted therefrom, and as a consequence, a space 43 is provided, enabling relatively free flow of air therethrough, greatly assisting the overall ventilation of the device.

The entire device is completely washable, repeatedly, without any damage or deteriorating effect on it.

While the cushion is preferably of pretreated sheepskin as identified at 36, it is also within the scope of the invention to use other materials for forming such cushion. FIG. 7 shows an alternate form of cushion 38, which is made up of a polyester blend material. This cushion is confined by a sheet 47 of nylon mesh stitched to the sleeve at 48. The sheet 47 is very porous, facilitating aeration. The cushion 38 in construction features, is similar to the cushion 36, i.e., of similar outline dimensions and thickness. This cushion also has the other attributes as described in connection with the cushion 28, as to washability, and ventilation.

Although the cushion, 36 or 38, is stitched to the material of the sleeve, the sleeve is nevertheless stretchable transversely within the end limits of the cushion for providing full flexibility of the hand. The cushion, and that portion of the sleeve to which it is secured, form an integral segment with the remainder of the material of the sleeve, in transverse directions.

What is claimed is:

1. A carpal tunnel protector for use on a person's hand, comprising, a tubular sleeve having a longitudinal direction and a transverse direction, and having a front end and a rear end, and being open at both ends, thereby forming end openings, the sleeve also having a side thumb hole near the front end, the sleeve forming front and rear leaves each having an inner surface and an outer surface, the sleeve being adapted to be worn on the hand and having such length as to reach from a position adjacent the middle of the palm of the hand, longitudinally, rearwardly beyond the palm of the hand and cover a portion of the wrist, with no parts extending forwardly beyond the middle of the palm of the hand during use, the sleeve including a body with binding strips thereon around the end openings and the thumb hole, the body being made up of woven material, and being of uniform construction throughout its entire extent, the sleeve being elastic in both longitudinal and transverse directions, and a single cushion secured only to the inner surface of the front leaf of the sleeve, the cushion including a single substantially rectangular member having a cover defining a single interior space with cushion material in the space, and completely filling the space and engaging the hand throughout the space, the cushion being so secured to the sleeve by stitching the cover only around its edges to the sleeve, and the cushion, as defined by its interior space, is so dimensioned as to completely cover the carpal tunnel both longitudinally and transversely, and the cushion material also extending rearwardly and covering a portion of the wrist, and, the binding strips being elastic and operable for yieldingly holding the sleeve against the hand and wrist of the bearer.

* * * * *